(12) United States Patent
Zhu et al.

(10) Patent No.: US 10,597,647 B2
(45) Date of Patent: Mar. 24, 2020

(54) COMPOSITIONS AND METHODS FOR IDENTIFYING HYDROXYMETHYLCYTOSINE IN A DNA

(71) Applicant: New England Biolabs, Inc., Ipswich, MA (US)

(72) Inventors: Zhenyu Zhu, Beverly, MA (US); Janine Borgaro, Beverly, MA (US); Aine Quimby, Newton, NH (US); Shengxi Guan, Stoneham, MA (US); Zhiyi Sun, Gloucester, MA (US)

(73) Assignee: New England Biolabs, Inc., Ipswich, MA (US)

( * ) Notice: Subject to any disclaimer, the term of this patent is extended or adjusted under 35 U.S.C. 154(b) by 368 days.

(21) Appl. No.: 14/317,143

(22) Filed: Jun. 27, 2014

(65) Prior Publication Data

US 2015/0004596 A1    Jan. 1, 2015

Related U.S. Application Data

(60) Provisional application No. 61/840,946, filed on Jun. 28, 2013.

(51) Int. Cl.
| | |
|---|---|
| *C12Q 1/68* | (2018.01) |
| *C12N 9/22* | (2006.01) |
| *C12Q 1/34* | (2006.01) |
| *C12Q 1/683* | (2018.01) |

(52) U.S. Cl.
CPC ............... *C12N 9/22* (2013.01); *C12Q 1/683* (2013.01)

(58) Field of Classification Search
CPC ............... C12Q 1/34; C12Q 1/68; C12N 9/22
See application file for complete search history.

(56) References Cited

U.S. PATENT DOCUMENTS

2012/0301881 A1    11/2012    Zhu et al.

FOREIGN PATENT DOCUMENTS

WO    WO 2011/091146 A1    7/2011

OTHER PUBLICATIONS

Borgaro, et al., Nucleic Acids Research, 41(7):4198-4206 (2013).
Wang, et al., Nucleic Acids Research, 39:9294-9305 (2011).
Sun, et al., Cell Reports, 3(2): 567-576 (2013).
Ehrlich, et al., Biochim Biophys Acta., 395(2):109-119 (1975).

*Primary Examiner* — Maryam Monshipouri
(74) *Attorney, Agent, or Firm* — New England Biolabs, Inc; Harriet M. Strimpel

(57) ABSTRACT

Provided herein in some embodiments is a non-naturally occurring variant of a wild type restriction enzyme defined by SEQ ID NO: 20, wherein the variant has at least a 2 fold increase in cleavage at 5-β glucosylhydroxymethylcytosine (5βghmC) compared with methylcytosine relative to the wild type enzyme. Methods for examining hydroxymethylation of a DNA sample using the variant enzyme are also provided.

12 Claims, 6 Drawing Sheets

Specification includes a Sequence Listing.

| | | | | |
|---|---|---|---|---|
| AbaDI | 251 | ITLKKLEEWKNGPQ------KRIVFARVKDNLSSRAMYRFMGLYEFQ----KADLKDGAVWKR | 303 | SEQ ID. No: 1 |
| AbaTI | 251 | ITLKKLEEWKNGPQ------KRIVFARVKDNLSSRAMYRFMGLYEFQ----KADLKDGAVWKR | 303 | SEQ ID. No: 2 |
| AbaAI | 251 | ITLKKLEEWKNGPQ------KRIVFARVKDNLSSRAMYRFMGLYEFQ----KADLKDGAVWKR | 303 | SEQ ID. No: 3 |
| AbaSI | 254 | ITLKKLEEWKNGPQ------KRIVFARVKDNLSSRAMYRFMGLYEFQ----KADLKDGAVWKR | 306 | SEQ ID. No: 4 |
| AbaCI | 251 | ITLKKLEEWKNGPQ------KRIVFARVKDNLSSRAMYRFMGLYEFQ----KADLKDGAVWKR | 306 | SEQ ID. No: 5 |
| AbaUI | 251 | ITLKKLEEWKNGPQ------KRIVFARVKDNLSSRAMYRFMGLYEFQ----KADLKDGAVWKR | 306 | SEQ ID. No: 6 |
| AbaBGI | 251 | ITLKKLEEWKNGPQ------KRIVFARVKDNLSSRAMYRFMGLYEFQ----KADLKDGAVWKR | 306 | SEQ ID. No: 7 |
| AbaHI | 251 | ITLKKLEEWKNGPQ------KRIVFARVKDNLNSRAMYRFMGLYKFQ----KADLKDGAVWKR | 306 | SEQ ID. No: 8 |
| AcaPI | 251 | ITLKKLEEWKNGPQ------KRIVFARVKDNLSSRAMYRFMGLYEFQ----KADLKDGAVWKR | 306 | SEQ ID. No: 9 |
| PpeHI | 235 | NNYIEDWD----------YRIVMAHSRDELN-RVLYRFLGVFQIDK--NKSVEGKNIFKR | 281 | SEQ ID. No: 10 |

FIG. 4

| | PpeHI | PpeHI R256G | AbaAI | AbaAI R279G | AbaUI | AbaUI R279G | AbaDI | AbaDI R279G | AbaSI | AbaSI R282G |
|---|---|---|---|---|---|---|---|---|---|---|
| Specific Activity on 5βghmC units/mg | 7.8K | 7.4K | 14.8K | 30K | 7.5K | 14K | 8.4K | 18.3K | 15.8K | 16.7K |
| Selectivity for 5βghmC over 5mC | 8X | 8000X | 2000X | 64000X | 1000X | 64000X | 256X | 16000X | 500X | 16000X |
| Fold difference between mutant and WT | 1000X | | 32X | | 64X | | 64X | | 32X | |

COMPOSITIONS AND METHODS FOR IDENTIFYING HYDROXYMETHYLCYTOSINE IN A DNA

CROSS-REFERENCING

This patent application claims the benefit of U.S. provisional application Ser. No. 61/840,946, filed on Jun. 28, 2013, which application is incorporated by reference herein.

GOVERNMENT RIGHTS

This invention was made with Government support under contract GM096723 awarded by the National Institutes of Health. The Government has certain rights in this invention.

BACKGROUND

A family of enzymes have been described that exhibits cleavage specificity toward 5-hydroxymethylcytosine (5 hmC) over 5-methylcytosine (5 mC) and cytosine (C) (for example, WO 2011/091146, US 2012/0301881, Borgaro, et al., *Nucleic Acids Research*, 41(7):4198-4206 (2013), Wang, et al. *Nucleic Acids Research*, 39:9294-9305 (2011)). Representative members of this family of enzymes have been used for high resolution mapping of genomic 5 hmC in mouse embryonic cells (Sun, et al., *Cell Reports*, 3(2):567-576 (2013)). AbaSI described first in US 2012/0301881 has specificity for hmCN11-13/N9-10G, preferring 5-β glucosylhydroxymethylcytosine (5βghmC) over 5 mC in a ratio of 500:1 and 8000:1 with KOAc at a final concentration of 250 mM, but with a loss of 75% in the activity (Wang, et al. (2011)).

In mammalian genomic DNA, the most abundant modification is 5 mC. 5 hmC is only a small part relative to 5 mC, from 0-25% depending on the tissue. It is desirable for a reagent to have greater selectivity for 5βghmC converted from 5 hmC by a β glucosyltransferase with 100% efficiency over 5 mC to reduce the background digestion from 5 mC when determining modification. Although the family of enzymes that include AbaSI is a discriminator of 5βghmC over 5 mC and C, it would be desirable to enhance the discrimination between 5βghmC and 5 mC/C.

SUMMARY

In general, a non-natural variant of a wild type restriction enzyme is provided wherein the wild type restriction enzyme is defined by SEQ ID NO: 20, and wherein the variant has at least 90% sequence identity to the wild type enzyme and has at least a 2 fold increase in cleavage at 5βghmC compared with 5 mC relative to the wild type enzyme.

In one aspect, the non-natural variant has one or more amino acid substitutions at a position corresponding to V72, T152 or R282 of SEQ ID NO:11, for example, the variant may have an amino acid substitution at a position corresponding to R282 of SEQ ID NO:11. In further examples, the substitution may be any amino acid except for F, Y, I, and V. In further examples, the substitution may be any of K, T, Q, L, S, M, C, N, G or A such as a G or A.

In one aspect, a DNA encoding a non-natural variant enzyme of the type described above is provided. The DNA may be included in a vector. A cell may also be provided having been transformed with a vector In general in one aspect, a method is provided that includes reacting a non-natural variant enzyme such as described above with a DNA comprising one or more of nucleotides selected from the group consisting of 5-β glucosylhydroxymethylcytosine (5βghmC) and hydroxymethylcytosine, for fragmenting the DNA.

In one aspect, the method includes determining at least one of the location of and the amount of 5 hmC or 5βghmC in the DNA. In another aspect, the method includes reacting the DNA with β glucosyltransferase (βGT) prior to reacting the variant enzyme with the DNA, thereby converting any hydroxymethylcytosines in the DNA to 5-β glucosylhydroxymethylcytosines.

In one aspect, the method may further include sequencing the DNA to create a hydroxymethylome map of the DNA for example where the DNA is part or all of a genome.

In another aspect, the method may include determining the presence or absence of 5 hmC or 5βghmC at a predetermined position in the DNA.

In general, a method is provided that includes obtaining a library of non-natural variants of a wild type restriction enzyme wherein the wild type restriction enzyme is defined by SEQ ID NO: 20, and wherein the variant has at least 90% sequence identity with SEQ ID NO:20; assaying for cleavage specificity of the variant enzymes for 5βGhmC and for 5 mC; and selecting a variant having at least 2 fold increase in selectivity for 5βghmC versus 5 mC compared to the wild type restriction enzyme.

In one aspect of the method, the variants may have one or more amino acid substitutions either within and/or outside of the amino acid sequence corresponding to SEQ ID NO:20 or SEQ ID NO:21.

BRIEF DESCRIPTION OF THE FIGURES

The abbreviations used herein are as follows: cytosine=C, 5-hydroxymethylcytosine=5 hmC, 5-methylcytosine=5 mC, 5-β glucosylhydroxymethylcytosine=5βghmC, 5 hmC in DNA modified by a mutant T4 glucosyltransferase=T4gt, 5 hmC in DNA modified by a T4 β glucosyltransferase=T4β, 5 hmC in DNA modified by a T4 α glucosyltransferase=T4α, wild type=WT.

Figures 1A, 1B:
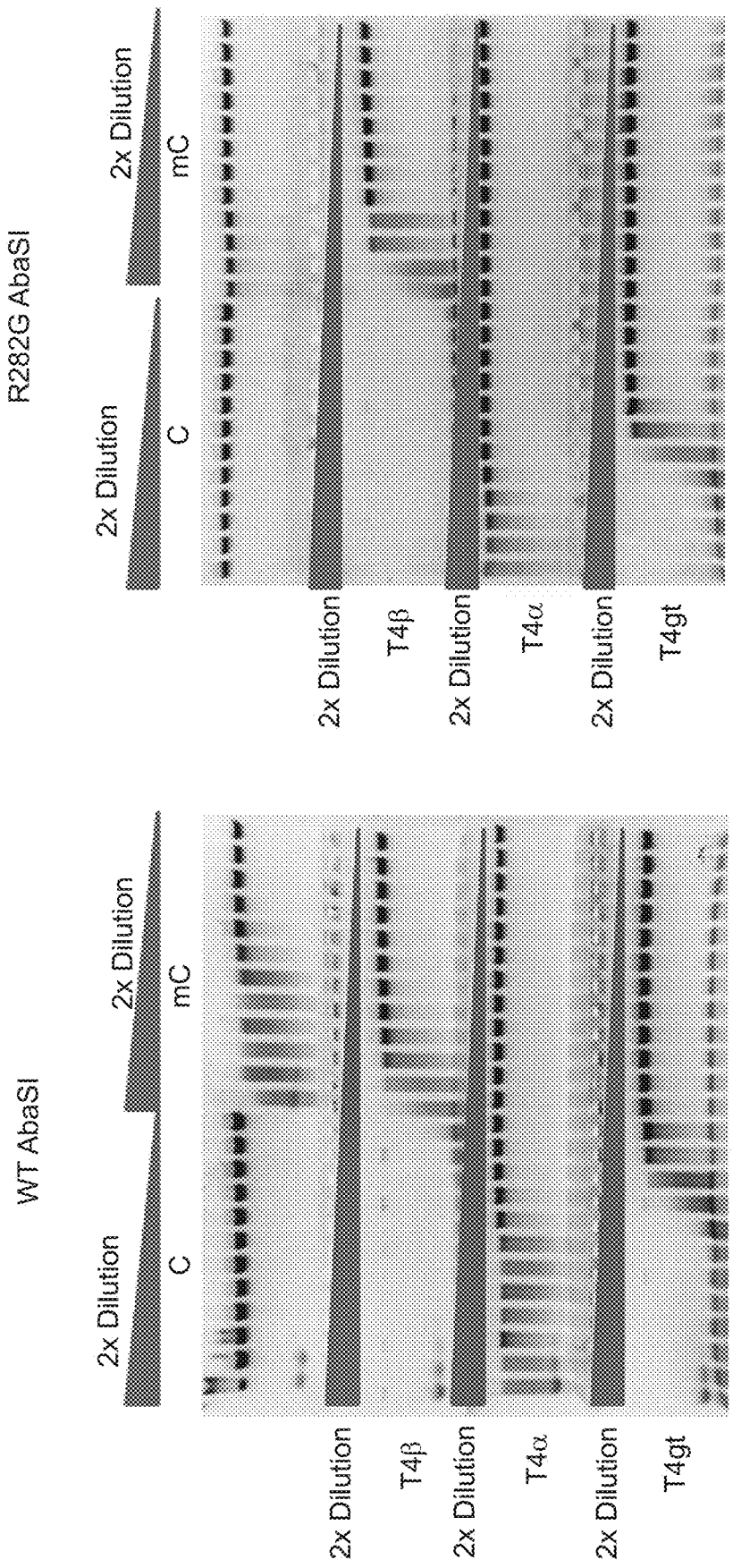
FIGS. 1A and 1B show the relative cleavage specificities of the AbaSI R282G mutant compared with the WT AbaSI on mutant phage T4gt DNA (all cytosines are non-glucosylated 5 hmC), phage T4β DNA (all cytosines are β-glucosylated 5 hmC), phage T4α DNA (all cytosines are α-glucosylated 5 hmC), phage XP12 DNA (all cytosines are methylated (5 mC)), and non-methylated lambda DNA (C) substrates.

The relative cleavage specificities for WT AbaSI as shown in FIG. 1A were C:mC:T4β:T4α:T4gt=ND:64:32000:128:2000. WT AbaSI has a 500 fold higher selectivity for T4β than for 5 mC.

The relative cleavage specificities for a R282G AbaSI mutant as shown in FIG. 1B were C:mC:T4β:T4α:T4gt=ND:1:16000:16:128. R282G. The AbaSI mutant has a 16,000 fold higher selectivity for T4βghmC than 5 mC.

Figure 2:
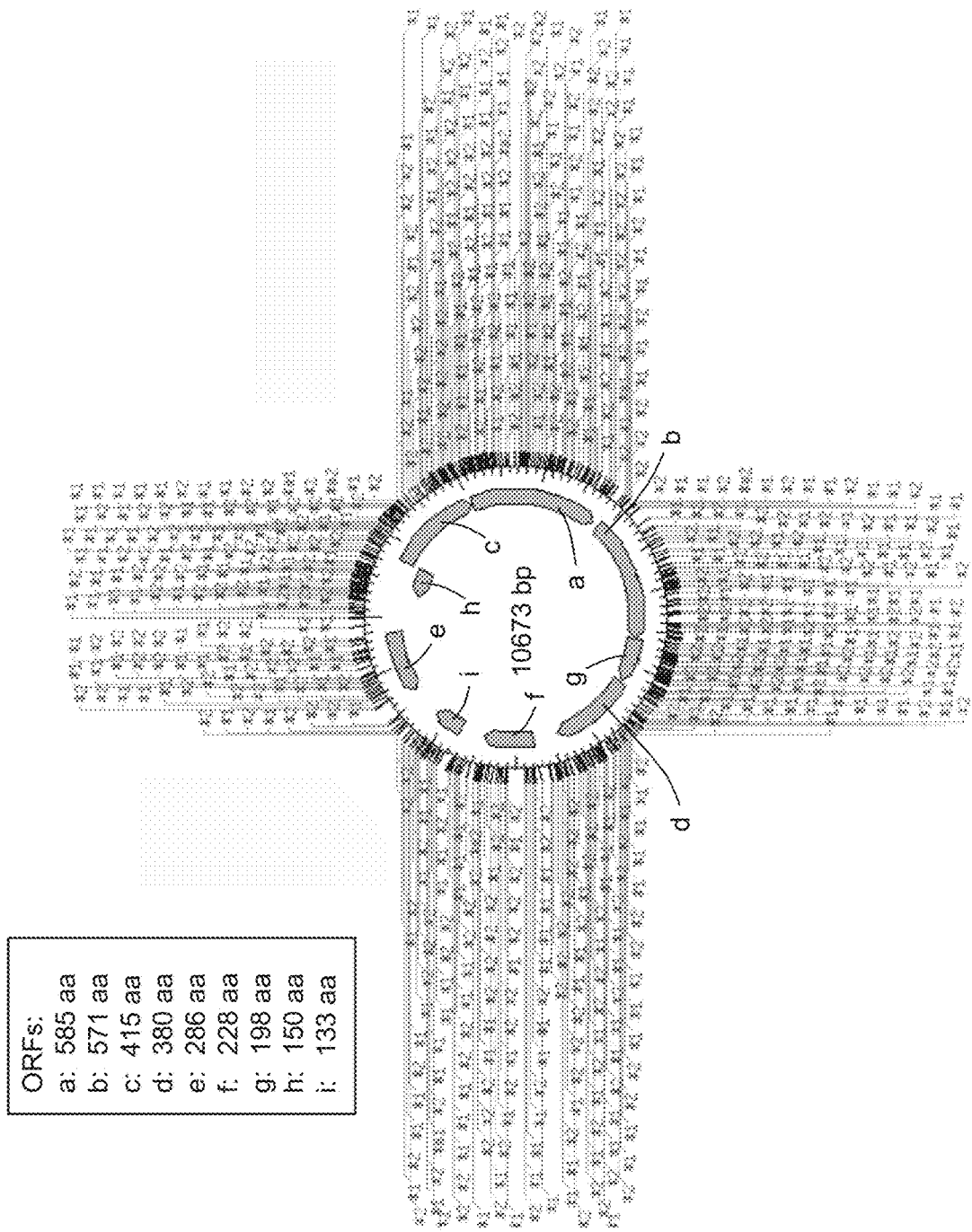

FIG. 2 shows 752×CG(N20/21)G site on pBC4 (New England Biolabs, Ipswich, Mass.) where CG is methylated using CpG methylase (M.SssI, New England Biolabs, Ipswich, Mass.). One cut on both strands of the plasmid substrate at any site linearizes the supercoiled plasmid. This is a sensitive assay to determine low activity digestion on 5 mC containing DNA. The higher the concentration of enzyme required to obtain linearized pBC4 relative to the digestion of 5βghmC, the more selective the enzyme for 5βghmC.

Figure 3A:
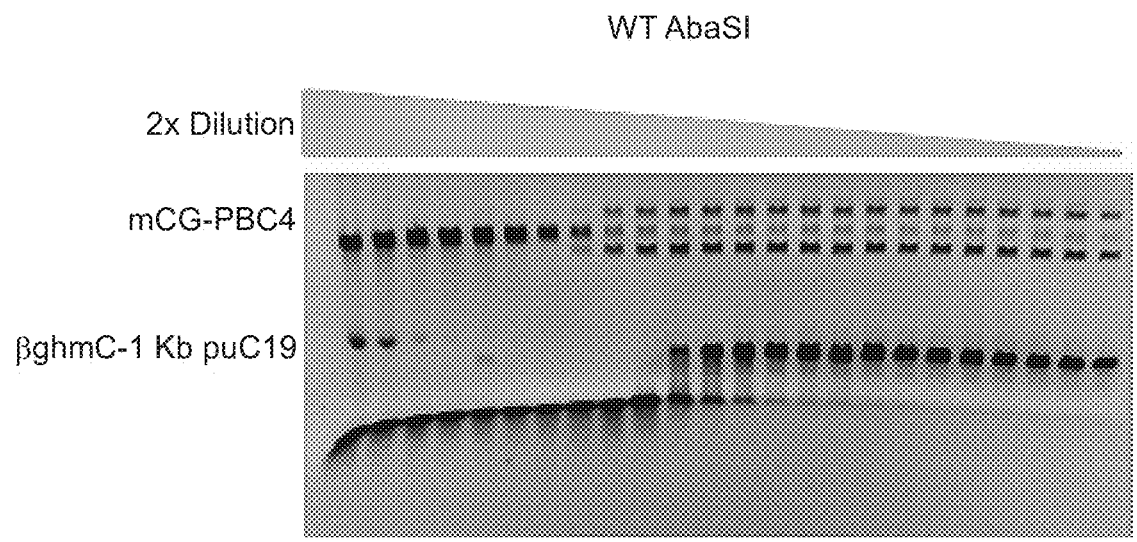
Figure 3B:
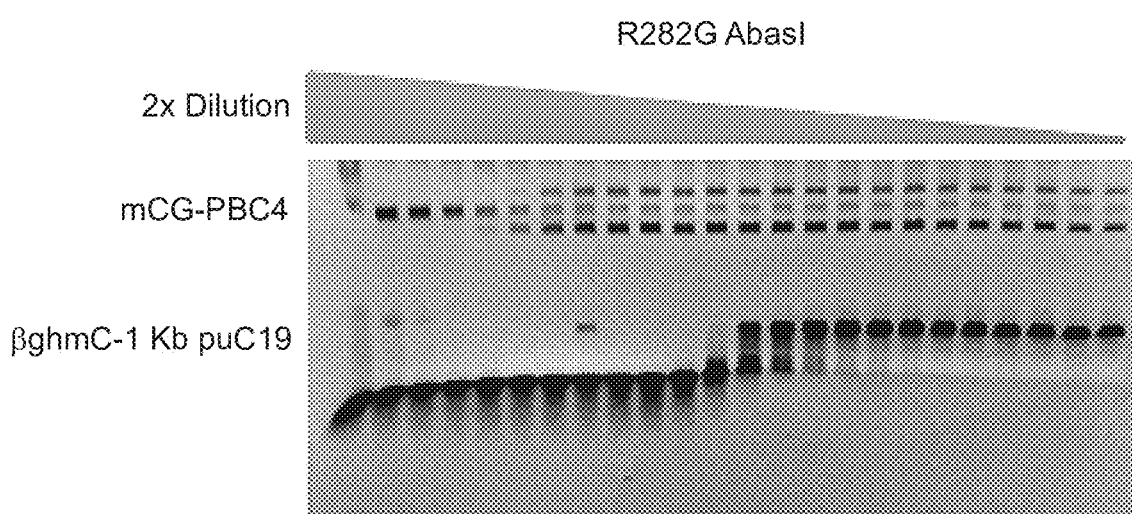

FIGS. 3A and 3B show assays demonstrating improved selectivity of a mutant AbaSI over WT enzyme for 5βghmC versus 5 mC.

Mutant AbaSI(R282G) has ⅛ of activity on mCG-PBC4, and 4 times more activity than WT AbaSI on 5βghmC. Consequently, the selectivity on 5βghmC over 5 mC is improved 32 times.

FIG. 4 shows a sequence alignment of about 50 amino acids in representative examples genes of Aba, Aca and PpeHI isolates showing that the sequence of these enzymes is highly conserved in this region. R279 corresponds to position 279 in SEQ ID NO:1 and is highlighted in SEQ ID NOs:1-10.

FIG. 5 provides a table showing that while activity of the mutants characterized in FIG. 4 is similar to the WT, the selectivity factor of the mutants for 5βghmC compared with 5 mC is significantly increased Mutants PpeHI(R256G), AbaAI(R279G), AbaUI(R279G) and AbaDI(R279G) and AbaSI(R282G) all showed significant improvement (32-1000 fold) in their selectivity toward 5βghmC over 5 mC when compared to the WT counterparts.

Figures 6A, 6B:
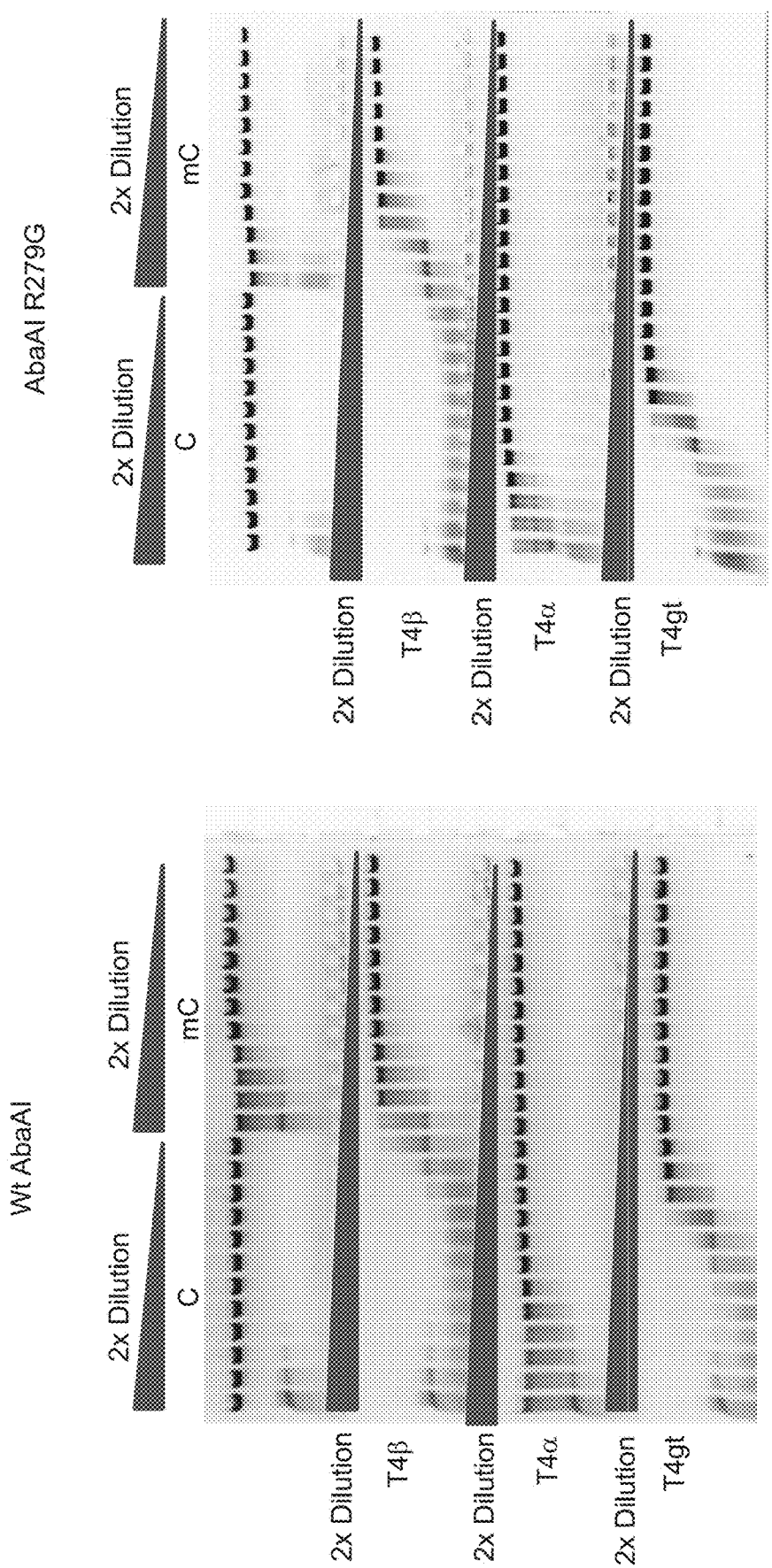

FIGS. 6A and 6B for mutant AbaAI(R279G) show the results of similar assays to those described in FIGS. 1A and 1B for mutant AbaSI(R282G) demonstrating improved selectivity of another mutant over WT enzyme for 5βghmC versus 5 mC.

DEFINITIONS

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., *Dictionary of Microbiology and Molecular Biology*, 2d Ed., John Wiley and Sons, New York (1994), and Hale & Markham, *The Harper Collins Dictionary of Biology*, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "an enzyme" refers to one or more enzymes, i.e., a single enzyme and multiple enzymes. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As used herein, the term "wild type" refers to a biopolymer (e.g., a protein or nucleic acid) that is the same as a biopolymer that exists in nature.

As used herein, the term "non-naturally occurring" refers to a biopolymer that does not exist in nature.

As used herein, the term "variant" refers to a protein that has one or more changes in its amino acid sequence (e.g., amino acid substitutions) relative to another enzyme, where the parent enzyme may exist in nature. Examples of variants are examples of enzymes that are not known to exist in nature and are the product of artificial design and synthesis. The term "mutant" is used interchangeably with the term "variant".

In certain cases, an enzyme may be referred to as being "defined by" a consensus sequence. For clarity, this phrase is intended to mean the enzyme has an amino acid sequence that falls into the scope of the consensus sequence.

As used herein, the term "increase in cleavage at 5βghmC compared with 5 mC" refers to an increase in the rate of cleavage of a DNA containing 5βghmC, relative the rate of cleavage of the same DNA containing 5 mC at the same position as the 5βghmC.

The term "corresponding positions" including grammatical equivalents thereof, refers to the same positions in a sequence when the sequences are aligned with one another using a sequence alignment program, e.g., BLAST.

As used herein, the term "reacting" refers to the act of combining elements together in the presence of all necessary reagents, e.g., buffer, salts and cofactors, in order to effect a biochemical reaction.

As used herein, the term "sequencing" refers to determining the identity of at least 10 contiguous nucleotides in a DNA molecule.

As used herein, the term "predetermined position" refers to a position that is known or targeted for analysis prior to performing an assay.

As used herein, the term "library" refers to a collection of different variants. A library can contain at least 2, at least 5, at least 10, at least 50 or at least 100 or members.

Other definitions of terms may appear throughout the specification.

DETAILED DESCRIPTION

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

The genome of *Acinetobacter baumannii* (Aba), *Acinetobacter calcoaceticus* (Aca) and *Proteus penneri* (PpeHI) express enzymes that are capable of cleaving 5 hmC and 5 ghmC but have substantially reduced cleavage activity for 5 mC and no detectable cleavage of C. Different isolates of these organisms have given rise to slight variations within the coding sequence of this enzyme. Although the various isolates share substantial sequence homology, mutations at the C-terminal end specifically resulted in improved selectivity without significant change in activity. Variants were created that contained mutations within and/or outside a conserved region of about 50 amino acids that may vary between isolates no more than an amount selected from 1%, 2%, 3%, 4%, 5%, 6%, 7%, 8%, 9% or 10%. Mutants were characterized by one, 2, 3, 4 or 5 or more amino acid changes compared with the WT sequence.

Mutants of the isolates were cloned and expressed and an improved activity and/or selectivity was identified. The improved activity was characterized by at least 2 fold, 3 fold, 4 fold, 5 fold, 6 fold, 7 fold, 8 fold, 9 fold or 10 fold increase in cleavage selectivity for 5βghmC compared with 5 mC when compared to WT enzyme.

Provided herein are non-naturally occurring variants of wild type restriction enzymes defined by SEQ ID NO:20. In some cases, a variant which may have at least 80% amino acid sequence identity (e.g., at least 85%, at least 90% or at least 95%) with the wild type enzyme (e.g., to any one of SEQ ID NOs: 1-11) also has at least a 2-fold increase (e.g., at least a 2-fold increase, or at least a 3-fold increase, or at least a 4-fold increase or at least a 5-fold increase, or at least a 10-fold increase) in cleavage at 5βghmC compared with 5 mC, relative to the wild type enzyme.

Examples of wild type enzymes of the same family as the *Acinetobacter baumannii* (Aba), *Acinetobacter calcoaceticus* (Aca) and *Proteus penneri* (PpeHI) enzymes exemplified herein include, but are not limited to, the sequences defined by the following Genbank accession numbers, which sequences are incorporated by reference herein: WP_000492972.1 (*Acinetobacter baumannii*), WP_000492974.1 (*Acinetobacter baumannii*), WP_002048156. (*Acinetobacter baumannii*), WP_014702593.1 (*Acinetobacter baumannii*), ETQ96741.1 (*Acinetobacter baumannii*), EXR87074.1 (*Acinetobacter baumannii*), WP_003294517.1 (*Acinetobacter baumannii*), WP_004744359.1 (*Acinetobacter baumannii*), WP_000492970.1 (*Acinetobacter baumannii*), WP_000492968.1 (*Acinetobacter baumannii*), EXD76626.1 (*Acinetobacter baumannii*), EXQ97018.1 (*Acinetobacter baumannii*), WP_025465614.1 *Acinetobacter baumannii*), WP_000492971.1 (*Acinetobacter baumannii*), WP_005038160.1 (*Acinetobacter calcoaceticus*), EXC95939.1(*Acinetobacter baumannii*), WP_016656853.1 (*Acinetobacter rudis*), WP_006533282.1 (*Proteus penneri*), EUD02953.1 (*Providencia Alcalifaciens*), WP_011039664.1 (*Proteus vulgaris*), 4OQ2_A (*Proteus vulgaris*), WP_021557107.1(*Enterobacteriaceae*), and WP_003826116.1(*Citrobacter freundii*). Further sequences in this family can be readily identified by performing a sequence comparison on a database or by hybridization.

The wild type consensus sequence of SEQ ID NO:20 resulted from analysis of several members of a family restriction enzymes that are structurally related to SEQ ID NO: 11 (AbaS1), as shown below.

```
AbaS1
                                   (SEQ ID NO: 12)
RIVFARVKDNLSSRAMYRFMGL

WP_005038160.1
                                   (SEQ ID NO: 13)
RIVFARVKDNLSSRAMYRFMGL

WP_000492971.1
                                   (SEQ ID NO: 14)
RIVFARVKDNLSSRAMYRFMGL

EXC95939.1
                                   (SEQ ID NO: 15)
RIVFARVKDNLNSRAMYSFMGL

WP_003826116.1
                                   (SEQ ID NO: 16)
RIVMAHSRDELN-RTLYRFLGV

EUD02953.1
                                   (SEQ ID NO: 17)
RIVMAHSRDELN-RTLYRFLGV

WP_011039664.1
                                   (SEQ ID NO: 18)
RIVMAHSRDELN-RTLYRFLGV

WP_006533282.1
                                   (SEQ ID NO: 19)
RIVMAHSRDELN-RVLYRFLGV
```

Written out, the consensus sequence that defines this family of proteins is RIVXAXXK/RDXLXO RXM/I/L/VYXFM/I/L/VGM/I/L/V, where X is any amino acid and O is S or no amino acid (SEQ ID NO:20). The amino acid corresponding to R282 in SEQ ID NO:11 is underlined in the consensus sequence.

In certain embodiments, the consensus sequence that defines this family of proteins is KRIVFARVKDNLXS RAMLYRFMGLYXFQ, where X is any amino acid (SEQ ID NO: 21). The amino acid corresponding to R282 in SEQ ID NO:11 is underlined in the consensus sequence.

The non-natural variant protein may have one or more amino acid substitutions within the consensus sequence or outside of the consensus sequence (SEQ ID NO:20 or SEQ ID NO: 21).

In certain embodiments, the non-natural variant has at least 90% sequence identity to a wild type restriction enzyme defined by SEQ ID NO:20 or SEQ ID NO:21, and has an amino acid substitution at a position corresponding to R282 of SEQ ID NO:11. In some cases, this non-natural variant may have at least a 2 fold increase in cleavage at 5βghmC compared with 5 mC relative to the wild type enzyme.

In certain embodiments, the non-natural variant has one or more amino acid substitutions at a position corresponding to V72, T152 or R282, relative to SEQ ID NO:11. In particular embodiments, the amino acid substitution may be at a position corresponding R282 of SEQ ID NO:11. In these embodiments, the position corresponding to R282 may be substituted with any amino acid except for F, Y, I, and V. For example, in some embodiments, the position corresponding to R282 may be substituted with K, T, Q, L, S, M, C, N, G or A, e.g., G or A.

A DNA encoding a non-natural variant enzyme is also provided. Because the genetic code and recombinant techniques for manipulating nucleic acids are known and the amino acid sequences of the variant enzymes are described herein, the design and production of nucleic acids encoding a variant enzyme used in the subject methods are well within the skill of an artisan. In certain embodiments, standard recombinant DNA technology (Ausubel, et al, Short *Protocols in Molecular Biology*, 5th ed., Wiley & Sons, 2002; Sambrook, et al., *Molecular Cloning: A Laboratory Manual*, 3d. ed., (2001) Cold Spring Harbor, N.Y.) methods are used. In certain embodiments, the nucleic acid may be codon optimized for expression in cells of a particular species, e.g., a particular species of bacteria.

A vector comprising a DNA encoding a non-natural variant enzyme, as well as a cell that has been transformed with such a vector, are also provided. Vectors and host cells are well known in the art.

Also provided herein is a method of digesting DNA using a non-natural variant enzyme. As noted above, a non-natural variant enzyme can cleave DNA that contains methylcytosine, hydroxymethylcytosine and 5-β glucosylhydroxymethylcytosine. In some embodiments, this method may involve reacting a variant enzyme with a DNA containing methylcytosine, cytosine and one or more of 5-β glucosylhydroxymethylcytosine (5βghmC) and hydroxymethylcytosine (depending on whether the DNA has been modified by treatment with β glucosyltransferase (βGT)), thereby fragmenting the DNA. In some cases, the DNA may be genomic DNA from a mammal, e.g., human genomic DNA, or a fragment of the same. In some cases, the DNA may have been enriched for methylated or hydroxymethylated sequences prior to digestion.

In some cases, after digestion, the method may further comprise determining the location and/or the amount of 5 hmC or 5βghmC in the DNA. In cases in which the DNA has been modified by treatment with β glucosyltransferase, digestion indicates that the initial DNA (prior to modification) contains one or more hydroxymethylcytosines.

In certain embodiments, the method may comprise sequencing the DNA to create a hydroxymethylome map of the DNA. The DNA may be all or a part of a genome, and, in certain cases, the method may comprise determining the presence or absence of 5 hmC or 5βghmC at a predetermined position in the DNA.

In some cases, this method may comprise reacting the DNA with β glucosyltransferase (βGT) prior to reacting the variant enzyme with the DNA, thereby converting any hydroxymethylcytosines in the DNA to 5-β glucosylhydroxymethylcytosines.

In some embodiments, two portions of the same sample: a first portion that has been treated with β glucosyltransferase and a second portion that has not been treated with β glucosyltransferase, may be digested, and the results may be compared to determine the location and/or amount of hydroxymethylated cytosines in the sample. In these embodiments, the extent of cleavage of a site may be measured quantitatively (e.g., using qPCR) to quantify the amount of hydroxymethylcytosine at a particular site.

Also provided herein is a screening method to identify other variants that have an increased specificity for 5βGhmC over 5 mC. In certain embodiments, this method may involve obtaining a library of non-naturally occurring variants of a wild type restriction enzyme defined by SEQ ID NO:20; assaying for cleavage specificity of the variant enzymes for 5βGhmC and for 5 mC; and selecting a variant having at least a 2-fold increase (e.g., at least a 4-fold increase, at least a 5-fold increase, or at least 10-fold increase in selectivity for 5βghmC versus 5 mC compared to the wild type restriction enzyme. In some embodiments, some of the non-naturally occurring variants screened in the assay may have one or more amino acid substitutions that are introduced into the amino acid sequence corresponding to SEQ ID NO:20.

All references cited herein are incorporated by reference.

EXAMPLES

Aspects of the present teachings can be further understood in light of the following examples, which should not be construed as limiting the scope of the present teachings in any way.

Example 1: Determination of Relative Selectivity and Activity of Mutants of Aba Isolates The cleavage of test substrate in which every C is a glucosylated hmC was determined for mutants from crude lysates using an assay procedure described in Wang, et al. (2011) for purified WT enzymes. Several mutant enzymes in which an amino acid has been changed at a position and type corresponding to V73A, T152A and/or R282A in SEQ ID NO:11 which showed higher activity than WT AbaSI (SEQ ID NO:11) were purified to homogeneity by the intein method described in Borgaro, et al. (2013). After purification, non-natural variant enzymes having a mutation at a site corresponding to R282 in SEQ ID NO: 11 were found to have much better selectivity on 5βghmC over 5 mC than the WT AbaSI. Whereas mutant enzymes with mutations corresponding to R282F, R282Y, R282I, or R282V (SEQ ID NO: 11), all showed cleavage activity with selectivity in the range of 500:1 (5βghmC:5 mC=500:1), similar to WT AbaSI, significant improvement in selectivity when compared with the WT isolates could be observed for non-natural variants having a mutation corresponding to the following positions in AbaSI, SEQ ID NO: 11 as follows: AbaSI. R282A showed selectivity of 5βghmC:5 mC=16000:1, R282K and R282T showed selectivity of 5βghmC:5 mC=2000:1. R282Q, R282L showed relative selectivity of 5βghmC:5 mC=8000:1. R282S, R282M, R282C, R282N and R282G showed relative selectivity similar to that of R282A of 5βghmC:5 mC=16000:1. FIG. 1B shows results for R282G which showed 32 times improved selectivity of 5βghmC over 5 mC than that of WT.

Example 2: Use of Different Substrates for Detecting Enzyme Cleavage Activity

In Example 1, a phage XP12 (Ehrlich, et al., *Biochim Biophys Acta.*, 395(2):109-119 (1975)) in which 5 mC completely replaces C was used as substrate. FIGS. 1A and 1B show the results obtained using this substrate in an assay to measure the relative activity of an AbaSI mutant. A positive result corresponds to cleavage of all 5 mC sites in the substrate.

An alternative sensitive assay utilized a supercoiled vector which has 752 mC site at a CG(N20-21)G (CpG methylated pBC4 (mCG-PBC4) (FIG. 2). When cleaved on both strands at any site, the vector was linearized. Only 1/64 amount of enzyme was required to completely linearize the mCG-PBC4 comparing to the amount for the complete digestion of XP12. A comparison of activity on mCG-PBC4 and 5βghmC showed that AbaSI (R282G) was 32 times higher than WT AbaSI on the selectivity on 5βghmC over 5mC (FIG. 3A-3B).

Example 3: Analysis of Mutant Enzymes

The R282 residue of AbaSI is conserved in among the homologous enzymes (FIG. 4). PpeHI(R256G) was also mutated at the corresponding residue (FIG. 5).

AbaAI(R279G), AbaUI(R279G) and AbaDI(R279G) and AbaSI(R282G) all showed significant improvement 32-64 fold in their selectivity toward 5βghmC over 5 mC when compared to the WT counterparts. The results for AbaAI (R279G) in FIG. 6B demonstrate the observed improved selectivity without loss of activity.

PpeHI(R256G), showed 1000 fold improvement in selectivity toward 5βghmC over 5 mC when compared to the WT counterparts.

AbaDI:
(SEQ ID NO: 22)
MFSSDLTDYVIRQLGRTKNKRYETYVVSRIIHLLNDFTLKFVTQQFVR
LSNKKIALTDLYFPQLGIHIEVDEEHHFLRNSKMEYSLNQIDEPLYSI
SHTESDAMREEDIISITGHKIFRVNVFKNQEGQPQNLESIHQQIDKII
EEIKTAKNKLIEASTFKEWNIETEYNPQTYIDLGRISLADNVVLKTTK
DVCNCFGYNYKNYQRGGALHPYKKDTLIWFPRLYENKDWINTISPDGL
TITEKSTDETITLKKLEEWKNGPQKRIVFARVKDNLSSRAMYRFMGLY
EFQKADLKDGAVWKRVECEVQTYSPKETKC

AbaTI:
(SEQ ID NO: 23)
MFSSDLTDYVIRQLGRTKNKRYETYVVSRIIHLLNDFTLKFVTQQFVR
LSNKKIALTDLYFPQLGIHIEVDEEHHFLRNSKMEYSLNQIDEPLYSI
SHTESDAMREEDIISITGHKIFRVNVFKNQEGQPQNLESIHQQIDKII
EEIKTAKNKLIEASTFKEWNIETEYNPQTYIDLGRISLADNVVLKTTK
DVCNCFGYNYKNYQRGGALHPYKKDTLIWFPRLYENKDWINTISPDGL
TITEKSTDETITLKKLEEWKNGPQKRIVFARVKDNLSSRAMYRFMGLY
EFQKADLKDGAVWKRVECEVQTYSPKETKC

AbaAI:
(SEQ ID NO: 24)
MFSSDLTDYVIRQLGRTKNKRYEAYVVSRIIHLLNDFTLKFVTQQFVR
LSNKKIALTDLYFPQLGIHIEVDEEHHFLRNSKMEYSLNQIDEPLYSI
SHTESDAMREEDIISITGHKIFRVNVFKNQEGQPQNLESIHQQIDKII
EKIKTAKNKLIEASTFKEWNIETEYNPQTYIDLGRISLADNVVLKTTK
DVCNCFGYNYKNYQRGGALHPYEKDTLIWFPRLYENKDWFNTISPDGL
TITEKSTDEAITLKKLEEWKNGPQKRIVFARVKDNLSSRAMYRFMGLY
EFQKADLKDGAVWKRVECEVQTYSPKETKC

AbaSI
(SEQ ID NO: 11)
MCNKASSDLTDYVIRQLGRTKNKRYEAYVVSRIIH LLNDFTLKFVTQ
QFVRLSNKKIALTDLYFPQLGIHIEVDEGHHFLRNSKMEYSLNQIDEP
LYSISQTESDAMREEDIISITGHKIFRVNVFKNQEGQPQNLENIHQQI
DKIIEEIKTAKNKLIEASTFKEWNIETEYNPQTYIDLGRISLADNVVL
KTTKDVCNCFGYSYKNYQRGGALHPYKKDTLIWFPRLYENKDWINTIS
PDGLTITEKSTDETITLKKLEEWKNGPQKRIVFARVKDNLSSRAMYRF
MGLYEFQKADLKDGAVWKRVKCEVQTYSPKETKC

AbaCI:
(SEQ ID NO: 25)
MFSSDLTDYVIRQLGRTKNKRYEAYVVSRIIHLLNDFTLKFVTQQFVR
LSNKKIALTDLYFPQLGIHIEVDEGHHFLRNSKMEYSLNQIDEPLYSI
SQTESDAMREEDIISITGHKIFRVNVFKNQEGQPQNLESIHQQIDKII
EEIKTAKNKLIEASTFKEWNIETEYNPQTYIDLGRISLADNVVLKTTK
DVCNCFGYNYKNYQRGGALHPYEKDTLIWFPRLYENKDWINTISPDGL
TITEKSTDETITLKKLEEWKNGPQKRIVFARVKDNLSSRAMYRFMGLY
EFQKADLKDGAVWKRVKCEVQTYSPKETKC

AbaUI:
(SEQ ID NO: 26)
MFSSDLTDYVIRQLGRTKNKRYEAYVVSRIIHLLNDITLKFVTQQFVR
LSNKKIALTDLYFPQLGIHIEVDEGHHFLRNSKMEYSLNQIDEPLYSI
SQTESDAMREEDIISITEHKIFRVNVYKNQEGQPQNLESIHQQIDKII
EEIKTAKNKLVEEFKFKEWNIETEYNPQTYIDLGRISLADNVVLKTTK
DVCNCFGYNYKNYQRGGALHPYEKDTLIWFPRLYENKDWINTISPDGL
TITEKSTDETITLKKLEEWKNGPQKRIVFARVKDNLSSRAMYRFMGLY
EFQKADLKDGAVWKRVKCEVQTYSPKETKC

AbaBGI:
(SEQ ID NO: 27)
MFSSDLTDYVIRQLGRTKNKRYEAYVVSRIIHLLNDFTLKFVTQQFVR
LSNKKIALTDLYFPQLGIHIEVDEGHHFLRNSKMEYSLNQIDEPLYSI
SQTESDAMREEDIISITGHKIFRVNVYKNQQGKPQNLESIHQQIDKII
EEIKTAKNKLIKASTFKEWNIETEYNPQTYIDLGRISLADNVVLKTTK
DVCNCFGYNYKNYQRGGALHPYEKDTLIWFPRLYENKDWINTISPDGL
TITEKSTDETITLKKLEEWKNGPQKRIVFARVKDNLSSRAMYRFMGLY
EFQKADLKDGAVWKRVKCEVQTYSPKETKC

AbaHI:
(SEQ ID NO: 28)
MFSSDLTDYVIRQLGRTKNKRYEAYVVSRIIHLLNDFTLKFVTQQFVR
LSNKKIALTDLYFPQLGIHIEVDEGHHFLRNSKMEYSLNQIDEPLYSI
SQTESDAMREEDIISITGHKIFRVNVYKNQEGQPQNLESIHQQIDKII
EEIKTAKNKLIEASTFKEWNIETEYNPQTYINLGRISLADNVVLKTTK
DVCNCFGYNYKNYQRGGAIHPYEEDTLIWFPRLYENKDWINTISPDGL
TITEKSTDETITLKKLEEWKNGPQKRIVFARVKDNLNSRAMYRFMGLY
KFQKADLKDGAVWKRVECEVQTYSPKETKC

AcaPI:
(SEQ ID NO: 29)
MFSSDLTDYVIRQLGRTKNKRYEAYVVSRIIHLLNDFTLKFVTQQFVR
LSNKKIALTDLYFPQLDIHIEVDEGHHFLRNSKMEYSLNQIDEPLYSI
SQTESDAMREEDIISITGHKIFRVNVYKNQEGEPQNLESIHQQIDKII
KEEIVAKNKQIKASTFKEWNIETEYNPQTYIDLGSISLADNVVLKTTK

-continued

DVCNCFGYNYKNYQRGGAIHPYEKDTLIWFPRLYENKDWINTISPDGL

TITEKSTDEAITLKKLEEWKNGPQKRIVFARVKDNLSSRAMYRFMGLY

EFQKADLKDGAVWKREGCKVQTYSPKEAKC

PpeHI:
(SEQ ID NO: 30)
MSKTDYILRSLSKITKKRWEHYVINRIFHKLDDPEIEFVCQQCIRKAN

SPDKIYLADLFFPQLALYLEIDEEHHDSDEAKKKDAKRRLDIIEATGF

-continued

IEKRIPASNVTIEQLNTSIDEFVKLLIDTKEKQKAQKKFIPWDYSAQY

TAKRHIDAGFIEVGPHAIFRYHRDALECFGYINKGHHQSGSWKLPENI

VREIGLSGRIMVVVFPRLYNAGVWNNELSPDGEWITEESLEVDNNYIE

DWDYRIVMAHSRDELNRVLYRFLGVFQIDKNKSVEGKNIFKRINTKVK

VFNSYN

What is claimed is:

1. A non-naturally occurring variant having at least 90% sequence identity to the corresponding wild type restriction enzyme in a family of related restriction endonucleases characterized by a consensus sequence of SEQ ID NO:21, wherein the variant has a mutation at one or more positions selected from positions corresponding to V72, T152 and R282 in SEQ ID NO: 11, and wherein the variant has at least a 2 fold increase in cleavage at 5-β glucosylhydroxymethylcytosine (5βghmC) compared with 5 methyl C (5mC) relative to the wild type enzyme.

2. The variant of claim 1, wherein the variant has an amino acid substitution at a position corresponding to R282 of SEQ ID NO:11.

3. The variant of claim 2, wherein the position corresponding to R282 of SEQ ID NO:11 is substituted with any amino acid except for F, Y, I, and V.

4. The variant of claim 2, wherein the position corresponding to R282 of SEQ ID NO:11 is substituted with K, T, Q, L, S, M, C, N, G or A.

5. The variant of claim 2, wherein the position corresponding to R282 of SEQ ID NO:11 is substituted with a G or A.

6. A method, comprising:
reacting a variant restriction enzyme of claim 1 with a DNA comprising one or more nucleotides selected from the group consisting of 5-β glucosylhydroxymethylcytosine (5βghmC) and hydroxymethylcytosine (hmC), for cleaving the DNA.

7. The method of claim 6, further comprising:
determining at least one of the location of and the amount of 5hmC or 5βghmC in the DNA.

8. The method of claim 6, wherein the method further comprises:
reacting the DNA with β glucosyltransferase (βGT) prior to reacting the variant enzyme with the DNA, thereby converting any hmC in the DNA to 5 βghmC.

9. The method of claim 6, further comprising:
sequencing the DNA to create a hydroxymethylome map of the DNA.

10. The method of claim 6, wherein the DNA is part or all of a genome.

11. The method of claim 6, wherein the method comprises determining the presence or absence of 5hmC or 5βghmC at a predetermined position in the DNA.

12. A method, comprising:
a. obtaining a library of non-naturally occurring variants having at least 90% sequence identity to the corresponding wild type restriction enzyme in a family of related restriction endonucleases characterized by a consensus sequence of SEQ ID NO:21, wherein the variant has a mutation at one or more positions selected from positions corresponding to V72, T152 and R282 in SEQ ID NO: 11, and wherein the variant has at least a 2 fold increase in cleavage at 5βghmC compared with 5mC relative to the wild type enzyme
b. assaying for cleavage specificity of the variant enzymes for 5βghmC and for 5mC; and
c. selecting a variant having at least 2 fold increase in selectivity for 5βghmC versus 5mC compared to the wild type restriction enzyme.

* * * * *

SEQUENCE LISTING

<160> NUMBER OF SEQ ID NOS: 30

<210> SEQ ID NO 1
<211> LENGTH: 53
<212> TYPE: PRT
<213> ORGANISM: Acinetobacter baumannii

<400> SEQUENCE: 1

Ile Thr Leu Lys Lys Leu Glu Glu Trp Lys Asn Gly Pro Gln Lys Arg
1               5                   10                  15

Ile Val Phe Ala Arg Val Lys Asp Asn Leu Ser Ser Arg Ala Met Tyr
            20                  25                  30

Arg Phe Met Gly Leu Tyr Glu Phe Gln Lys Ala Asp Leu Lys Asp Gly
        35                  40                  45

Ala Val Trp Lys Arg
    50

<210> SEQ ID NO 2
<211> LENGTH: 53
<212> TYPE: PRT
<213> ORGANISM: Acinetobacter baumannii

<400> SEQUENCE: 2

Ile Thr Leu Lys Lys Leu Glu Glu Trp Lys Asn Gly Pro Gln Lys Arg
1               5                   10                  15

Ile Val Phe Ala Arg Val Lys Asp Asn Leu Ser Ser Arg Ala Met Tyr
            20                  25                  30

Arg Phe Met Gly Leu Tyr Glu Phe Gln Lys Ala Asp Leu Lys Asp Gly
        35                  40                  45

Ala Val Trp Lys Arg
    50

<210> SEQ ID NO 3
<211> LENGTH: 53
<212> TYPE: PRT
<213> ORGANISM: Acinetobacter baumannii

<400> SEQUENCE: 3

Ile Thr Leu Lys Lys Leu Glu Glu Trp Lys Asn Gly Pro Gln Lys Arg
1               5                   10                  15

Ile Val Phe Ala Arg Val Lys Asp Asn Leu Ser Ser Arg Ala Met Tyr
            20                  25                  30

Arg Phe Met Gly Leu Tyr Glu Phe Gln Lys Ala Asp Leu Lys Asp Gly
        35                  40                  45

Ala Val Trp Lys Arg
    50

<210> SEQ ID NO 4

<211> LENGTH: 53
<212> TYPE: PRT
<213> ORGANISM: Acinetobacter baumannii

<400> SEQUENCE: 4

Ile Thr Leu Lys Lys Leu Glu Glu Trp Lys Asn Gly Pro Gln Lys Arg
1               5                   10                  15

Ile Val Phe Ala Arg Val Lys Asp Asn Leu Ser Ser Arg Ala Met Tyr
            20                  25                  30

Arg Phe Met Gly Leu Tyr Glu Phe Gln Lys Ala Asp Leu Lys Asp Gly
        35                  40                  45

Ala Val Trp Lys Arg
    50

<210> SEQ ID NO 5
<211> LENGTH: 53
<212> TYPE: PRT
<213> ORGANISM: Acinetobacter baumannii

<400> SEQUENCE: 5

Ile Thr Leu Lys Lys Leu Glu Glu Trp Lys Asn Gly Pro Gln Lys Arg
1               5                   10                  15

Ile Val Phe Ala Arg Val Lys Asp Asn Leu Ser Ser Arg Ala Met Tyr
            20                  25                  30

Arg Phe Met Gly Leu Tyr Glu Phe Gln Lys Ala Asp Leu Lys Asp Gly
        35                  40                  45

Ala Val Trp Lys Arg
    50

<210> SEQ ID NO 6
<211> LENGTH: 53
<212> TYPE: PRT
<213> ORGANISM: Acinetobacter baumannii

<400> SEQUENCE: 6

Ile Thr Leu Lys Lys Leu Glu Glu Trp Lys Asn Gly Pro Gln Lys Arg
1               5                   10                  15

Ile Val Phe Ala Arg Val Lys Asp Asn Leu Ser Ser Arg Ala Met Tyr
            20                  25                  30

Arg Phe Met Gly Leu Tyr Glu Phe Gln Lys Ala Asp Leu Lys Asp Gly
        35                  40                  45

Ala Val Trp Lys Arg
    50

<210> SEQ ID NO 7
<211> LENGTH: 53
<212> TYPE: PRT
<213> ORGANISM: Acinetobacter baumannii

<400> SEQUENCE: 7

Ile Thr Leu Lys Lys Leu Glu Glu Trp Lys Asn Gly Pro Gln Lys Arg
1               5                   10                  15

Ile Val Phe Ala Arg Val Lys Asp Asn Leu Ser Ser Arg Ala Met Tyr
            20                  25                  30

Arg Phe Met Gly Leu Tyr Glu Phe Gln Lys Ala Asp Leu Lys Asp Gly
        35                  40                  45

Ala Val Trp Lys Arg
    50

```
<210> SEQ ID NO 8
<211> LENGTH: 53
<212> TYPE: PRT
<213> ORGANISM: Acinetobacter baumannii

<400> SEQUENCE: 8

Ile Thr Leu Lys Lys Leu Glu Glu Trp Lys Asn Gly Pro Gln Lys Arg
1               5                   10                  15

Ile Val Phe Ala Arg Val Lys Asp Asn Leu Asn Ser Arg Ala Met Tyr
            20                  25                  30

Arg Phe Met Gly Leu Tyr Lys Phe Gln Lys Ala Asp Leu Lys Asp Gly
        35                  40                  45

Ala Val Trp Lys Arg
    50

<210> SEQ ID NO 9
<211> LENGTH: 53
<212> TYPE: PRT
<213> ORGANISM: Acinetobacter calcoaceticus

<400> SEQUENCE: 9

Ile Thr Leu Lys Lys Leu Glu Glu Trp Lys Asn Gly Pro Gln Lys Arg
1               5                   10                  15

Ile Val Phe Ala Arg Val Lys Asp Asn Leu Ser Ser Arg Ala Met Tyr
            20                  25                  30

Arg Phe Met Gly Leu Tyr Glu Phe Gln Lys Ala Asp Leu Lys Asp Gly
        35                  40                  45

Ala Val Trp Lys Arg
    50

<210> SEQ ID NO 10
<211> LENGTH: 47
<212> TYPE: PRT
<213> ORGANISM: Proteus penneri

<400> SEQUENCE: 10

Asn Asn Tyr Ile Glu Asp Trp Asp Tyr Arg Ile Val Met Ala His Ser
1               5                   10                  15

Arg Asp Glu Leu Asn Arg Val Leu Tyr Arg Phe Leu Gly Val Phe Gln
            20                  25                  30

Ile Asp Lys Asn Lys Ser Val Glu Gly Lys Asn Ile Phe Lys Arg
        35                  40                  45

<210> SEQ ID NO 11
<211> LENGTH: 321
<212> TYPE: PRT
<213> ORGANISM: Acinetobacter baumannii

<400> SEQUENCE: 11

Met Cys Asn Lys Ala Ser Ser Asp Leu Thr Asp Tyr Val Ile Arg Gln
1               5                   10                  15

Leu Gly Arg Thr Lys Asn Lys Arg Tyr Glu Ala Tyr Val Val Ser Arg
            20                  25                  30

Ile Ile His Leu Leu Asn Asp Phe Thr Leu Lys Phe Val Thr Gln Gln
        35                  40                  45

Phe Val Arg Leu Ser Asn Lys Lys Ile Ala Leu Thr Asp Leu Tyr Phe
    50                  55                  60

Pro Gln Leu Gly Ile His Ile Val Asp Glu Gly His His Phe Leu
65                  70                  75                  80
```

-continued

Arg Asn Ser Lys Met Glu Tyr Ser Leu Asn Gln Ile Asp Glu Pro Leu
            85                  90                  95

Tyr Ser Ile Ser Gln Thr Glu Ser Asp Ala Met Arg Glu Glu Asp Ile
        100                 105                 110

Ile Ser Ile Thr Gly His Lys Ile Phe Arg Val Asn Val Phe Lys Asn
        115                 120                 125

Gln Glu Gly Gln Pro Gln Asn Leu Glu Asn Ile His Gln Gln Ile Asp
    130                 135                 140

Lys Ile Ile Glu Glu Ile Lys Thr Ala Lys Asn Lys Leu Ile Glu Ala
145                 150                 155                 160

Ser Thr Phe Lys Glu Trp Asn Ile Glu Thr Glu Tyr Asn Pro Gln Thr
                165                 170                 175

Tyr Ile Asp Leu Gly Arg Ile Ser Leu Ala Asp Asn Val Val Leu Lys
            180                 185                 190

Thr Thr Lys Asp Val Cys Asn Cys Phe Gly Tyr Ser Tyr Lys Asn Tyr
        195                 200                 205

Gln Arg Gly Gly Ala Leu His Pro Tyr Lys Lys Asp Thr Leu Ile Trp
    210                 215                 220

Phe Pro Arg Leu Tyr Glu Asn Lys Asp Trp Ile Asn Thr Ile Ser Pro
225                 230                 235                 240

Asp Gly Leu Thr Ile Thr Glu Lys Ser Thr Asp Glu Thr Ile Thr Leu
                245                 250                 255

Lys Lys Leu Glu Glu Trp Lys Asn Gly Pro Gln Lys Arg Ile Val Phe
            260                 265                 270

Ala Arg Val Lys Asp Asn Leu Ser Ser Arg Ala Met Tyr Arg Phe Met
        275                 280                 285

Gly Leu Tyr Glu Phe Gln Lys Ala Asp Leu Lys Asp Gly Ala Val Trp
    290                 295                 300

Lys Arg Val Lys Cys Glu Val Gln Thr Tyr Ser Pro Lys Glu Thr Lys
305                 310                 315                 320

Cys

<210> SEQ ID NO 12
<211> LENGTH: 22
<212> TYPE: PRT
<213> ORGANISM: Acinetobacter baumannii

<400> SEQUENCE: 12

Arg Ile Val Phe Ala Arg Val Lys Asp Asn Leu Ser Ser Arg Ala Met
1               5                   10                  15

Tyr Arg Phe Met Gly Leu
            20

<210> SEQ ID NO 13
<211> LENGTH: 22
<212> TYPE: PRT
<213> ORGANISM: Acinetobacter calcoaceticus

<400> SEQUENCE: 13

Arg Ile Val Phe Ala Arg Val Lys Asp Asn Leu Ser Ser Arg Ala Met
1               5                   10                  15

Tyr Arg Phe Met Gly Leu
            20

<210> SEQ ID NO 14
<211> LENGTH: 22
<212> TYPE: PRT

<213> ORGANISM: Acinetobacter baumannii

<400> SEQUENCE: 14

Arg Ile Val Phe Ala Arg Val Lys Asp Asn Leu Ser Ser Arg Ala Met
1               5                   10                  15

Tyr Arg Phe Met Gly Leu
            20

<210> SEQ ID NO 15
<211> LENGTH: 22
<212> TYPE: PRT
<213> ORGANISM: Acinetobacter baumannii

<400> SEQUENCE: 15

Arg Ile Val Phe Ala Arg Val Lys Asp Asn Leu Asn Ser Arg Ala Met
1               5                   10                  15

Tyr Ser Phe Met Gly Leu
            20

<210> SEQ ID NO 16
<211> LENGTH: 22
<212> TYPE: PRT
<213> ORGANISM: Citrobacter freundii
<220> FEATURE:
<221> NAME/KEY: MISC_FEATURE
<222> LOCATION: (13)..(13)
<223> OTHER INFORMATION: Xaa can be S or no amino acid

<400> SEQUENCE: 16

Arg Ile Val Met Ala His Ser Arg Asp Glu Leu Asn Xaa Arg Thr Leu
1               5                   10                  15

Tyr Arg Phe Leu Gly Val
            20

<210> SEQ ID NO 17
<211> LENGTH: 22
<212> TYPE: PRT
<213> ORGANISM: Providencia alcalifaciens
<220> FEATURE:
<221> NAME/KEY: MISC_FEATURE
<222> LOCATION: (13)..(13)
<223> OTHER INFORMATION: Xaa can be S or no amino acid

<400> SEQUENCE: 17

Arg Ile Val Met Ala His Ser Arg Asp Glu Leu Asn Xaa Arg Thr Leu
1               5                   10                  15

Tyr Arg Phe Leu Gly Val
            20

<210> SEQ ID NO 18
<211> LENGTH: 22
<212> TYPE: PRT
<213> ORGANISM: Proteus vulgaris
<220> FEATURE:
<221> NAME/KEY: MISC_FEATURE
<222> LOCATION: (13)..(13)
<223> OTHER INFORMATION: Xaa can be S or no amino acid

<400> SEQUENCE: 18

Arg Ile Val Met Ala His Ser Arg Asp Glu Leu Asn Xaa Arg Thr Leu
1               5                   10                  15

Tyr Arg Phe Leu Gly Val
            20

```
<210> SEQ ID NO 19
<211> LENGTH: 22
<212> TYPE: PRT
<213> ORGANISM: Proteus penneri
<220> FEATURE:
<221> NAME/KEY: MISC_FEATURE
<222> LOCATION: (13)..(13)
<223> OTHER INFORMATION: Xaa can be S or no amino acid

<400> SEQUENCE: 19

Arg Ile Val Met Ala His Ser Arg Asp Glu Leu Asn Xaa Arg Val Leu
1               5                   10                  15

Tyr Arg Phe Leu Gly Val
            20

<210> SEQ ID NO 20
<211> LENGTH: 22
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)..(4)
<223> OTHER INFORMATION: Xaa can be any naturally occuring amino acid
<220> FEATURE:
<221> NAME/KEY: misc_feature
<222> LOCATION: (6)..(7)
<223> OTHER INFORMATION: Xaa can be any naturally occuring amino acid
<220> FEATURE:
<221> NAME/KEY: misc_feature
<222> LOCATION: (8)..(8)
<223> OTHER INFORMATION: Xaa can be M, I, L or V
<220> FEATURE:
<221> NAME/KEY: misc_feature
<222> LOCATION: (10)..(10)
<223> OTHER INFORMATION: Xaa can be any naturally occuring amino acid
<220> FEATURE:
<221> NAME/KEY: misc_feature
<222> LOCATION: (12)..(12)
<223> OTHER INFORMATION: Xaa can be any naturally occuring amino acid
<220> FEATURE:
<221> NAME/KEY: misc_feature
<222> LOCATION: (13)..(13)
<223> OTHER INFORMATION: Xaa can be S or no amino acid
<220> FEATURE:
<221> NAME/KEY: misc_feature
<222> LOCATION: (15)..(15)
<223> OTHER INFORMATION: Xaa can be any naturally occuring amino acid
<220> FEATURE:
<221> NAME/KEY: misc_feature
<222> LOCATION: (16)..(16)
<223> OTHER INFORMATION: Xaa can be M, I, L or V
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be M, I, L or V
<220> FEATURE:
<221> NAME/KEY: misc_feature
<222> LOCATION: (22)..(22)
<223> OTHER INFORMATION: Xaa can be M, I, L or V

<400> SEQUENCE: 20

Arg Ile Val Xaa Ala Xaa Xaa Xaa Asp Xaa Leu Xaa Xaa Arg Xaa Xaa
1               5                   10                  15

Tyr Xaa Phe Xaa Gly Xaa
            20

<210> SEQ ID NO 21
```

```
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (13)..(13)
<223> OTHER INFORMATION: Xaa can be any naturally occuring amino acid
<220> FEATURE:
<221> NAME/KEY: MISC_FEATURE
<222> LOCATION: (26)..(26)
<223> OTHER INFORMATION: Xaa can be any naturally occuring amino acid

<400> SEQUENCE: 21

Lys Arg Ile Val Phe Ala Arg Val Lys Asp Asn Leu Xaa Ser Arg Ala
1               5                   10                  15

Met Leu Tyr Arg Phe Met Gly Leu Tyr Xaa Phe Gln
            20                  25

<210> SEQ ID NO 22
<211> LENGTH: 318
<212> TYPE: PRT
<213> ORGANISM: Acinetobacter baumannii

<400> SEQUENCE: 22

Met Phe Ser Ser Asp Leu Thr Asp Tyr Val Ile Arg Gln Leu Gly Arg
1               5                   10                  15

Thr Lys Asn Lys Arg Tyr Glu Thr Tyr Val Val Ser Arg Ile Ile His
            20                  25                  30

Leu Leu Asn Asp Phe Thr Leu Lys Phe Val Thr Gln Gln Phe Val Arg
        35                  40                  45

Leu Ser Asn Lys Lys Ile Ala Leu Thr Asp Leu Tyr Phe Pro Gln Leu
    50                  55                  60

Gly Ile His Ile Glu Val Asp Glu Glu His His Phe Leu Arg Asn Ser
65                  70                  75                  80

Lys Met Glu Tyr Ser Leu Asn Gln Ile Asp Pro Leu Tyr Ser Ile
                85                  90                  95

Ser His Thr Glu Ser Asp Ala Met Arg Glu Glu Asp Ile Ile Ser Ile
            100                 105                 110

Thr Gly His Lys Ile Phe Arg Val Asn Val Phe Lys Asn Gln Glu Gly
        115                 120                 125

Gln Pro Gln Asn Leu Glu Ser Ile His Gln Gln Ile Asp Lys Ile Ile
    130                 135                 140

Glu Glu Ile Lys Thr Ala Lys Asn Lys Leu Ile Glu Ala Ser Thr Phe
145                 150                 155                 160

Lys Glu Trp Asn Ile Glu Thr Glu Tyr Asn Pro Gln Thr Tyr Ile Asp
                165                 170                 175

Leu Gly Arg Ile Ser Leu Ala Asp Asn Val Val Leu Lys Thr Thr Lys
            180                 185                 190

Asp Val Cys Asn Cys Phe Gly Tyr Asn Tyr Lys Asn Tyr Gln Arg Gly
        195                 200                 205

Gly Ala Leu His Pro Tyr Lys Lys Asp Thr Leu Ile Trp Phe Pro Arg
    210                 215                 220

Leu Tyr Glu Asn Lys Asp Trp Ile Asn Thr Ile Ser Pro Asp Gly Leu
225                 230                 235                 240

Thr Ile Thr Glu Lys Ser Thr Asp Glu Thr Ile Thr Leu Lys Lys Leu
                245                 250                 255

Glu Glu Trp Lys Asn Gly Pro Gln Lys Arg Ile Val Phe Ala Arg Val
```

```
            260                 265                 270
Lys Asp Asn Leu Ser Ser Arg Ala Met Tyr Arg Phe Met Gly Leu Tyr
        275                 280                 285
Glu Phe Gln Lys Ala Asp Leu Lys Asp Gly Ala Val Trp Lys Arg Val
    290                 295                 300
Glu Cys Glu Val Gln Thr Tyr Ser Pro Lys Glu Thr Lys Cys
305                 310                 315

<210> SEQ ID NO 23
<211> LENGTH: 318
<212> TYPE: PRT
<213> ORGANISM: Acinetobacter baumannii

<400> SEQUENCE: 23

Met Phe Ser Ser Asp Leu Thr Asp Tyr Val Ile Arg Gln Leu Gly Arg
1               5                   10                  15
Thr Lys Asn Lys Arg Tyr Glu Thr Tyr Val Val Ser Arg Ile Ile His
            20                  25                  30
Leu Leu Asn Asp Phe Thr Leu Lys Phe Val Thr Gln Gln Phe Val Arg
        35                  40                  45
Leu Ser Asn Lys Lys Ile Ala Leu Thr Asp Leu Tyr Phe Pro Gln Leu
    50                  55                  60
Gly Ile His Ile Glu Val Asp Glu His His Phe Leu Arg Asn Ser
65                  70                  75                  80
Lys Met Glu Tyr Ser Leu Asn Gln Ile Asp Glu Pro Leu Tyr Ser Ile
                85                  90                  95
Ser His Thr Glu Ser Asp Ala Met Arg Glu Asp Ile Ile Ser Ile
            100                 105                 110
Thr Gly His Lys Ile Phe Arg Val Asn Val Phe Lys Asn Gln Glu Gly
        115                 120                 125
Gln Pro Gln Asn Leu Glu Ser Ile His Gln Ile Asp Lys Ile Ile
    130                 135                 140
Glu Glu Ile Lys Thr Ala Lys Asn Lys Leu Ile Glu Ala Ser Thr Phe
145                 150                 155                 160
Lys Glu Trp Asn Ile Glu Thr Glu Tyr Asn Pro Gln Thr Tyr Ile Asp
                165                 170                 175
Leu Gly Arg Ile Ser Leu Ala Asp Asn Val Val Leu Lys Thr Thr Lys
            180                 185                 190
Asp Val Cys Asn Cys Phe Gly Tyr Asn Tyr Lys Asn Tyr Gln Arg Gly
        195                 200                 205
Gly Ala Leu His Pro Tyr Lys Lys Asp Thr Leu Ile Trp Phe Pro Arg
    210                 215                 220
Leu Tyr Glu Asn Lys Asp Trp Ile Asn Thr Ile Ser Pro Asp Gly Leu
225                 230                 235                 240
Thr Ile Thr Glu Lys Ser Thr Asp Glu Thr Ile Thr Leu Lys Lys Leu
                245                 250                 255
Glu Glu Trp Lys Asn Gly Pro Gln Lys Arg Ile Val Phe Ala Arg Val
            260                 265                 270
Lys Asp Asn Leu Ser Ser Arg Ala Met Tyr Arg Phe Met Gly Leu Tyr
        275                 280                 285
Glu Phe Gln Lys Ala Asp Leu Lys Asp Gly Ala Val Trp Lys Arg Val
    290                 295                 300
Glu Cys Glu Val Gln Thr Tyr Ser Pro Lys Glu Thr Lys Cys
305                 310                 315
```

<210> SEQ ID NO 24
<211> LENGTH: 318
<212> TYPE: PRT
<213> ORGANISM: Acinetobacter baumannii

<400> SEQUENCE: 24

```
Met Phe Ser Ser Asp Leu Thr Asp Tyr Val Ile Arg Gln Leu Gly Arg
1               5                   10                  15

Thr Lys Asn Lys Arg Tyr Glu Ala Tyr Val Ser Arg Ile Ile His
            20                  25                  30

Leu Leu Asn Asp Phe Thr Leu Lys Phe Val Thr Gln Gln Phe Val Arg
            35                  40                  45

Leu Ser Asn Lys Lys Ile Ala Leu Thr Asp Leu Tyr Phe Pro Gln Leu
        50                  55                  60

Gly Ile His Ile Glu Val Asp Glu Glu His His Phe Leu Arg Asn Ser
65                  70                  75                  80

Lys Met Glu Tyr Ser Leu Asn Gln Ile Asp Glu Pro Leu Tyr Ser Ile
                85                  90                  95

Ser His Thr Glu Ser Asp Ala Met Arg Glu Glu Asp Ile Ile Ser Ile
            100                 105                 110

Thr Gly His Lys Ile Phe Arg Val Asn Val Phe Lys Asn Gln Glu Gly
        115                 120                 125

Gln Pro Gln Asn Leu Glu Ser Ile His Gln Ile Asp Lys Ile Ile
    130                 135                 140

Glu Lys Ile Lys Thr Ala Lys Asn Lys Leu Ile Glu Ala Ser Thr Phe
145                 150                 155                 160

Lys Glu Trp Asn Ile Glu Thr Glu Tyr Asn Pro Gln Thr Tyr Ile Asp
                165                 170                 175

Leu Gly Arg Ile Ser Leu Ala Asp Asn Val Val Leu Lys Thr Thr Lys
            180                 185                 190

Asp Val Cys Asn Cys Phe Gly Tyr Asn Tyr Lys Asn Tyr Gln Arg Gly
        195                 200                 205

Gly Ala Leu His Pro Tyr Glu Lys Asp Thr Leu Ile Trp Phe Pro Arg
    210                 215                 220

Leu Tyr Glu Asn Lys Asp Trp Phe Asn Thr Ile Ser Pro Asp Gly Leu
225                 230                 235                 240

Thr Ile Thr Glu Lys Ser Thr Asp Glu Ala Ile Thr Leu Lys Lys Leu
                245                 250                 255

Glu Glu Trp Lys Asn Gly Pro Gln Lys Arg Ile Val Phe Ala Arg Val
            260                 265                 270

Lys Asp Asn Leu Ser Ser Arg Ala Met Tyr Arg Phe Met Gly Leu Tyr
        275                 280                 285

Glu Phe Gln Lys Ala Asp Leu Lys Asp Gly Ala Val Trp Lys Arg Val
    290                 295                 300

Glu Cys Glu Val Gln Thr Tyr Ser Pro Lys Glu Thr Lys Cys
305                 310                 315
```

<210> SEQ ID NO 25
<211> LENGTH: 318
<212> TYPE: PRT
<213> ORGANISM: Acinetobacter baumannii

<400> SEQUENCE: 25

```
Met Phe Ser Ser Asp Leu Thr Asp Tyr Val Ile Arg Gln Leu Gly Arg
1               5                   10                  15
```

Thr Lys Asn Lys Arg Tyr Glu Ala Tyr Val Ser Arg Ile Ile His
            20                  25                  30

Leu Leu Asn Asp Phe Thr Leu Lys Phe Val Thr Gln Gln Phe Val Arg
        35                  40                  45

Leu Ser Asn Lys Lys Ile Ala Leu Thr Asp Leu Tyr Phe Pro Gln Leu
    50                  55                  60

Gly Ile His Ile Glu Val Asp Glu Gly His His Phe Leu Arg Asn Ser
65                  70                  75                  80

Lys Met Glu Tyr Ser Leu Asn Gln Ile Asp Pro Leu Tyr Ser Ile
                85                  90                  95

Ser Gln Thr Glu Ser Asp Ala Met Arg Glu Asp Ile Ile Ser Ile
            100                 105                 110

Thr Gly His Lys Ile Phe Arg Val Asn Val Phe Lys Asn Gln Glu Gly
        115                 120                 125

Gln Pro Gln Asn Leu Glu Ser Ile His Gln Gln Ile Asp Lys Ile Ile
    130                 135                 140

Glu Glu Ile Lys Thr Ala Lys Asn Lys Leu Ile Glu Ala Ser Thr Phe
145                 150                 155                 160

Lys Glu Trp Asn Ile Glu Thr Glu Tyr Asn Pro Gln Thr Tyr Ile Asp
                165                 170                 175

Leu Gly Arg Ile Ser Leu Ala Asp Asn Val Val Leu Lys Thr Thr Lys
            180                 185                 190

Asp Val Cys Asn Cys Phe Gly Tyr Asn Tyr Lys Asn Tyr Gln Arg Gly
        195                 200                 205

Gly Ala Leu His Pro Tyr Glu Lys Asp Thr Leu Ile Trp Phe Pro Arg
    210                 215                 220

Leu Tyr Glu Asn Lys Asp Trp Ile Asn Thr Ile Ser Pro Asp Gly Leu
225                 230                 235                 240

Thr Ile Thr Glu Lys Ser Thr Asp Glu Thr Ile Thr Leu Lys Lys Leu
                245                 250                 255

Glu Glu Trp Lys Asn Gly Pro Gln Lys Arg Ile Val Phe Ala Arg Val
            260                 265                 270

Lys Asp Asn Leu Ser Ser Arg Ala Met Tyr Arg Phe Met Gly Leu Tyr
    275                 280                 285

Glu Phe Gln Lys Ala Asp Leu Lys Asp Gly Ala Val Trp Lys Arg Val
290                 295                 300

Lys Cys Glu Val Gln Thr Tyr Ser Pro Lys Glu Thr Lys Cys
305                 310                 315

<210> SEQ ID NO 26
<211> LENGTH: 318
<212> TYPE: PRT
<213> ORGANISM: Acinetobacter baumannii

<400> SEQUENCE: 26

Met Phe Ser Ser Asp Leu Thr Asp Tyr Val Ile Arg Gln Leu Gly Arg
1               5                   10                  15

Thr Lys Asn Lys Arg Tyr Glu Ala Tyr Val Ser Arg Ile Ile His
            20                  25                  30

Leu Leu Asn Asp Ile Thr Leu Lys Phe Val Thr Gln Gln Phe Val Arg
        35                  40                  45

Leu Ser Asn Lys Lys Ile Ala Leu Thr Asp Leu Tyr Phe Pro Gln Leu
    50                  55                  60

Gly Ile His Ile Glu Val Asp Glu Gly His His Phe Leu Arg Asn Ser
65                  70                  75                  80

Lys Met Glu Tyr Ser Leu Asn Gln Ile Asp Glu Pro Leu Tyr Ser Ile
                85                  90                  95

Ser Gln Thr Glu Ser Asp Ala Met Arg Glu Asp Ile Ile Ser Ile
            100                 105                 110

Thr Glu His Lys Ile Phe Arg Val Asn Val Tyr Lys Asn Gln Glu Gly
        115                 120                 125

Gln Pro Gln Asn Leu Glu Ser Ile His Gln Gln Ile Asp Lys Ile Ile
    130                 135                 140

Glu Glu Ile Lys Thr Ala Lys Asn Lys Leu Val Glu Phe Lys Phe
145                 150                 155                 160

Lys Glu Trp Asn Ile Glu Thr Glu Tyr Asn Pro Gln Thr Tyr Ile Asp
                165                 170                 175

Leu Gly Arg Ile Ser Leu Ala Asp Asn Val Val Leu Lys Thr Thr Lys
            180                 185                 190

Asp Val Cys Asn Cys Phe Gly Tyr Asn Tyr Lys Asn Tyr Gln Arg Gly
        195                 200                 205

Gly Ala Leu His Pro Tyr Glu Lys Asp Thr Leu Ile Trp Phe Pro Arg
    210                 215                 220

Leu Tyr Glu Asn Lys Asp Trp Ile Asn Thr Ile Ser Pro Asp Gly Leu
225                 230                 235                 240

Thr Ile Thr Glu Lys Ser Thr Asp Glu Thr Ile Thr Leu Lys Lys Leu
                245                 250                 255

Glu Glu Trp Lys Asn Gly Pro Gln Lys Arg Ile Val Phe Ala Arg Val
            260                 265                 270

Lys Asp Asn Leu Ser Ser Arg Ala Met Tyr Arg Phe Met Gly Leu Tyr
        275                 280                 285

Glu Phe Gln Lys Ala Asp Leu Lys Asp Gly Ala Val Trp Lys Arg Val
    290                 295                 300

Lys Cys Glu Val Gln Thr Tyr Ser Pro Lys Glu Thr Lys Cys
305                 310                 315

<210> SEQ ID NO 27
<211> LENGTH: 318
<212> TYPE: PRT
<213> ORGANISM: Acinetobacter baumannii

<400> SEQUENCE: 27

Met Phe Ser Ser Asp Leu Thr Asp Tyr Val Ile Arg Gln Leu Gly Arg
1               5                   10                  15

Thr Lys Asn Lys Arg Tyr Glu Ala Tyr Val Val Ser Arg Ile Ile His
            20                  25                  30

Leu Leu Asn Asp Phe Thr Leu Lys Phe Val Thr Gln Gln Phe Val Arg
        35                  40                  45

Leu Ser Asn Lys Lys Ile Ala Leu Thr Asp Leu Tyr Phe Pro Gln Leu
    50                  55                  60

Gly Ile His Ile Glu Val Asp Glu Gly His His Phe Leu Arg Asn Ser
65                  70                  75                  80

Lys Met Glu Tyr Ser Leu Asn Gln Ile Asp Glu Pro Leu Tyr Ser Ile
                85                  90                  95

Ser Gln Thr Glu Ser Asp Ala Met Arg Glu Asp Ile Ile Ser Ile
            100                 105                 110

Thr Gly His Lys Ile Phe Arg Val Asn Val Tyr Lys Asn Gln Gln Gly
        115                 120                 125

Lys Pro Gln Asn Leu Glu Ser Ile His Gln Gln Ile Asp Lys Ile Ile

```
            130                 135                 140
Glu Glu Ile Lys Thr Ala Lys Asn Lys Leu Ile Lys Ala Ser Thr Phe
145                 150                 155                 160

Lys Glu Trp Asn Ile Glu Thr Glu Tyr Asn Pro Gln Thr Tyr Ile Asp
                165                 170                 175

Leu Gly Arg Ile Ser Leu Ala Asp Asn Val Val Leu Lys Thr Thr Lys
            180                 185                 190

Asp Val Cys Asn Cys Phe Gly Tyr Asn Tyr Lys Asn Tyr Gln Arg Gly
                195                 200                 205

Gly Ala Leu His Pro Tyr Glu Lys Asp Thr Leu Ile Trp Phe Pro Arg
            210                 215                 220

Leu Tyr Glu Asn Lys Asp Trp Ile Asn Thr Ile Ser Pro Asp Gly Leu
225                 230                 235                 240

Thr Ile Thr Glu Lys Ser Thr Asp Glu Thr Ile Thr Leu Lys Lys Leu
                245                 250                 255

Glu Glu Trp Lys Asn Gly Pro Gln Lys Arg Ile Val Phe Ala Arg Val
                260                 265                 270

Lys Asp Asn Leu Ser Ser Arg Ala Met Tyr Arg Phe Met Gly Leu Tyr
                275                 280                 285

Glu Phe Gln Lys Ala Asp Leu Lys Asp Gly Ala Val Trp Lys Arg Val
            290                 295                 300

Lys Cys Glu Val Gln Thr Tyr Ser Pro Lys Glu Thr Lys Cys
305                 310                 315

<210> SEQ ID NO 28
<211> LENGTH: 318
<212> TYPE: PRT
<213> ORGANISM: Acinetobacter baumannii

<400> SEQUENCE: 28

Met Phe Ser Ser Asp Leu Thr Asp Tyr Val Ile Arg Gln Leu Gly Arg
1               5                   10                  15

Thr Lys Asn Lys Arg Tyr Glu Ala Tyr Val Val Ser Arg Ile Ile His
                20                  25                  30

Leu Leu Asn Asp Phe Thr Leu Lys Phe Val Thr Gln Gln Phe Val Arg
            35                  40                  45

Leu Ser Asn Lys Lys Ile Ala Leu Thr Asp Leu Tyr Phe Pro Gln Leu
        50                  55                  60

Gly Ile His Ile Glu Val Asp Glu Gly His His Phe Leu Arg Asn Ser
65                  70                  75                  80

Lys Met Glu Tyr Ser Leu Asn Gln Ile Asp Glu Pro Leu Tyr Ser Ile
                85                  90                  95

Ser Gln Thr Glu Ser Asp Ala Met Arg Glu Glu Asp Ile Ile Ser Ile
            100                 105                 110

Thr Gly His Lys Ile Phe Arg Val Asn Val Tyr Lys Asn Gln Glu Gly
            115                 120                 125

Gln Pro Gln Asn Leu Glu Ser Ile His Gln Ile Asp Lys Ile Ile
            130                 135                 140

Glu Glu Ile Lys Thr Ala Lys Asn Lys Leu Ile Glu Ala Ser Thr Phe
145                 150                 155                 160

Lys Glu Trp Asn Ile Glu Thr Glu Tyr Asn Pro Gln Thr Tyr Ile Asn
                165                 170                 175

Leu Gly Arg Ile Ser Leu Ala Asp Asn Val Val Leu Lys Thr Thr Lys
            180                 185                 190
```

```
Asp Val Cys Asn Cys Phe Gly Tyr Asn Tyr Lys Asn Tyr Gln Arg Gly
            195                 200                 205

Gly Ala Ile His Pro Tyr Glu Glu Asp Thr Leu Ile Trp Phe Pro Arg
        210                 215                 220

Leu Tyr Glu Asn Lys Asp Trp Ile Asn Thr Ile Ser Pro Asp Gly Leu
225                 230                 235                 240

Thr Ile Thr Glu Lys Ser Thr Asp Glu Thr Ile Thr Leu Lys Lys Leu
                245                 250                 255

Glu Glu Trp Lys Asn Gly Pro Gln Lys Arg Ile Val Phe Ala Arg Val
            260                 265                 270

Lys Asp Asn Leu Asn Ser Arg Ala Met Tyr Arg Phe Met Gly Leu Tyr
        275                 280                 285

Lys Phe Gln Lys Ala Asp Leu Lys Asp Gly Ala Val Trp Lys Arg Val
    290                 295                 300

Glu Cys Glu Val Gln Thr Tyr Ser Pro Lys Glu Thr Lys Cys
305                 310                 315

<210> SEQ ID NO 29
<211> LENGTH: 318
<212> TYPE: PRT
<213> ORGANISM: Acinetobacter calcoaceticus

<400> SEQUENCE: 29

Met Phe Ser Ser Asp Leu Thr Asp Tyr Val Ile Arg Gln Leu Gly Arg
1               5                   10                  15

Thr Lys Asn Lys Arg Tyr Glu Ala Tyr Val Val Ser Arg Ile Ile His
            20                  25                  30

Leu Leu Asn Asp Phe Thr Leu Lys Phe Val Thr Gln Gln Phe Val Arg
        35                  40                  45

Leu Ser Asn Lys Lys Ile Ala Leu Thr Asp Leu Tyr Phe Pro Gln Leu
    50                  55                  60

Asp Ile His Ile Glu Val Asp Glu Gly His His Phe Leu Arg Asn Ser
65                  70                  75                  80

Lys Met Glu Tyr Ser Leu Asn Gln Ile Asp Glu Pro Leu Tyr Ser Ile
                85                  90                  95

Ser Gln Thr Glu Ser Asp Ala Met Arg Glu Glu Asp Ile Ile Ser Ile
            100                 105                 110

Thr Gly His Lys Ile Phe Arg Val Asn Val Tyr Lys Asn Gln Glu Gly
        115                 120                 125

Glu Pro Gln Asn Leu Glu Ser Ile His Gln Gln Ile Asp Lys Ile Ile
    130                 135                 140

Glu Glu Ile Lys Val Ala Lys Asn Lys Gln Ile Lys Ala Ser Thr Phe
145                 150                 155                 160

Lys Glu Trp Asn Ile Glu Thr Glu Tyr Asn Pro Gln Thr Tyr Ile Asp
                165                 170                 175

Leu Gly Ser Ile Ser Leu Ala Asp Asn Val Val Leu Lys Thr Thr Lys
            180                 185                 190

Asp Val Cys Asn Cys Phe Gly Tyr Asn Tyr Lys Asn Tyr Gln Arg Gly
        195                 200                 205

Gly Ala Ile His Pro Tyr Glu Lys Asp Thr Leu Ile Trp Phe Pro Arg
    210                 215                 220

Leu Tyr Glu Asn Lys Asp Trp Ile Asn Thr Ile Ser Pro Asp Gly Leu
225                 230                 235                 240

Thr Ile Thr Glu Lys Ser Thr Asp Glu Ala Ile Thr Leu Lys Lys Leu
                245                 250                 255
```

```
Glu Glu Trp Lys Asn Gly Pro Gln Lys Arg Ile Val Phe Ala Arg Val
            260                 265                 270

Lys Asp Asn Leu Ser Ser Arg Ala Met Tyr Arg Phe Met Gly Leu Tyr
        275                 280                 285

Glu Phe Gln Lys Ala Asp Leu Lys Asp Gly Ala Val Trp Lys Arg Glu
290                 295                 300

Gly Cys Lys Val Gln Thr Tyr Ser Pro Lys Glu Ala Lys Cys
305                 310                 315

<210> SEQ ID NO 30
<211> LENGTH: 293
<212> TYPE: PRT
<213> ORGANISM: Proteus penneri

<400> SEQUENCE: 30

Met Ser Lys Thr Asp Tyr Ile Leu Arg Ser Leu Ser Lys Ile Thr Lys
1               5                   10                  15

Lys Arg Trp Glu His Tyr Val Ile Asn Arg Ile Phe His Lys Leu Asp
            20                  25                  30

Asp Pro Glu Ile Glu Phe Val Cys Gln Gln Cys Ile Arg Lys Ala Asn
        35                  40                  45

Ser Pro Asp Lys Ile Tyr Leu Ala Asp Leu Phe Phe Pro Gln Leu Ala
50                  55                  60

Leu Tyr Leu Glu Ile Asp Glu Glu His His Asp Ser Asp Glu Ala Lys
65                  70                  75                  80

Lys Lys Asp Ala Lys Arg Arg Leu Asp Ile Ile Glu Ala Thr Gly Phe
            85                  90                  95

Ile Glu Lys Arg Ile Pro Ala Ser Asn Val Thr Ile Glu Gln Leu Asn
        100                 105                 110

Thr Ser Ile Asp Glu Phe Val Lys Leu Leu Ile Asp Thr Lys Glu Lys
    115                 120                 125

Gln Lys Ala Gln Lys Lys Phe Ile Pro Trp Asp Tyr Ser Ala Gln Tyr
    130                 135                 140

Thr Ala Lys Arg His Ile Asp Ala Gly Phe Ile Glu Val Gly Pro His
145                 150                 155                 160

Ala Ile Phe Arg Tyr His Arg Asp Ala Leu Glu Cys Phe Gly Tyr Ile
                165                 170                 175

Asn Lys Gly His His Gln Ser Gly Ser Trp Lys Leu Pro Glu Asn Ile
            180                 185                 190

Val Arg Glu Ile Gly Leu Ser Gly Arg Ile Met Val Trp Phe Pro Arg
        195                 200                 205

Leu Tyr Asn Ala Gly Val Trp Asn Asn Glu Leu Ser Pro Asp Gly Glu
    210                 215                 220

Trp Ile Thr Glu Glu Ser Leu Glu Val Asp Asn Asn Tyr Ile Glu Asp
225                 230                 235                 240

Trp Asp Tyr Arg Ile Val Met Ala His Ser Arg Asp Glu Leu Asn Arg
                245                 250                 255

Val Leu Tyr Arg Phe Leu Gly Val Phe Gln Ile Asp Lys Asn Lys Ser
            260                 265                 270

Val Glu Gly Lys Asn Ile Phe Lys Arg Ile Asn Thr Lys Val Lys Val
        275                 280                 285

Phe Asn Ser Tyr Asn
    290
```